US010093595B2

(12) United States Patent
Choi et al.

(10) Patent No.: US 10,093,595 B2
(45) Date of Patent: Oct. 9, 2018

(54) CONCURRENT REDUCTION FOR IMPROVING THE PERFORMANCE OF THE DEHYDROGENATION OF ALKANES

(71) Applicant: SABIC GLOBAL TECHNOLOGIES B.V., Bergen op Zoom (NL)

(72) Inventors: YongMan Choi, Riyadh (SA); Ramsey Bunama, Riyadh (SA); Khalid M. El-Yahyaoui, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/528,971

(22) PCT Filed: Nov. 25, 2015

(86) PCT No.: PCT/IB2015/059118
§ 371 (c)(1),
(2) Date: May 23, 2017

(87) PCT Pub. No.: WO2016/084012
PCT Pub. Date: Jun. 2, 2016

(65) Prior Publication Data
US 2017/0267607 A1 Sep. 21, 2017

Related U.S. Application Data

(60) Provisional application No. 62/085,234, filed on Nov. 26, 2014.

(51) Int. Cl.
| | | |
|---|---|---|
| *C07C 5/333* | (2006.01) | |
| *B01J 38/04* | (2006.01) | |
| *B01J 23/26* | (2006.01) | |
| *B01J 23/92* | (2006.01) | |
| *C09K 5/16* | (2006.01) | |

(52) U.S. Cl.
CPC ............ *C07C 5/3332* (2013.01); *B01J 23/26* (2013.01); *B01J 23/92* (2013.01); *B01J 38/04* (2013.01); *C09K 5/16* (2013.01); *C07C 2523/26* (2013.01); *Y02P 20/146* (2015.11); *Y02P 20/584* (2015.11)

(58) Field of Classification Search
CPC ... C07C 5/3332; C07C 2523/26; C07C 11/02; C07C 11/09; C07C 5/3335
See application file for complete search history.

(56) References Cited

U.S. PATENT DOCUMENTS

| | | | |
|---|---|---|---|
| 2,500,482 A | 3/1950 | Barter | |
| 7,973,207 B2 | 7/2011 | Fridman et al. | |
| 8,188,328 B2 | 5/2012 | Fridman et al. | |
| 2005/0124840 A1* | 6/2005 | Chen .................. | C07C 5/48 585/658 |
| 2008/0097134 A1 | 4/2008 | Fridman et al. | |

FOREIGN PATENT DOCUMENTS

| | | |
|---|---|---|
| CN | 102531817 A | 7/2012 |
| DE | 1815773 A1 | 7/1969 |
| WO | 2005060442 A2 | 7/2005 |

OTHER PUBLICATIONS

Cavani et al. "Chemical and Physical Characterization of Alumina-Suppored Chromia-Based Catalysts and Their Activity in Dehydrogenation of Isobutane", Journal of Catalysis, 1996, vol. 158, pp. 236-250.
Fridman et al.; "New HGM Concept of Non-Oxidative Dehydrogenation for Houdry Technology"; Proceeding of 23rd North American Catalysis Society Meeting; 2013; 1 Page.
International Search Report for International Application No. PCT/IB2015/059118; International Filing Date: Nov. 25, 2015; dated Feb. 15, 2016; 5 Pages.
Liu et al. "Converting of Carbon Dioxide into More Valuable Chemical using Catalytic Plasmas," Fuels, 45(4), 694-697.
Machine Translation of CN102531817(A); Date of Publication: Jul. 4, 2012; 25 Pages.
Machine Translation of DE1815773(A1); Date of Publication: Jul. 24, 1969; 3 Pages.
Neugebauer et al. "The Heat of Formation of Ammonium Dichromate", The Journal of Physical Chemistry, 1957, vol. 61, pp. 1429-1430.
Written Opinion of the International Searching Authority for International Application No. PCT/IB2015/059118; International Filing Date: Nov. 25, 2015; dated Feb. 15, 2016; 5 Pages.

* cited by examiner

*Primary Examiner* — Sharon Pregler
(74) *Attorney, Agent, or Firm* — Cantor Colburn LLP

(57) ABSTRACT

A process of catalytically dehydrogenating an alkane to an alkene, using $Cr_2O_3$ as a catalyst, where the catalyst is reduced concurrently with the dehydrogenation by using CO as a reducing gas. In reducing the catalyst with CO, $CO_2$ is produced, which may be reacted with $H_2$ produced by the dehydrogenation, to form CO and $H_2O$ by the reverse water-gas shift reaction. A Cu O heat-releasing material may be included with the catalyst in the reactor. The CO reducing gas reduces CuO to form Cu and $CO_2$, releasing heat. The $CO_2$ produced by reducing the Cu O may also be reacted with $H_2$ produced by the dehydrogenation, to form CO and $H_2O$ by the reverse water-gas shift reaction.

19 Claims, 2 Drawing Sheets

CONCURRENT REDUCTION FOR IMPROVING THE PERFORMANCE OF THE DEHYDROGENATION OF ALKANES

CROSS REFERENCE TO RELATED APPLICATIONS

This application is a 371 of International Application No. PCT/IB2015/059118, filed Nov 25, 2015, which claims priority to U.S. application Ser. No. 62/085,234, filed Nov. 26, 2014 which are incorporated herein by reference in their entirety.

BACKGROUND FIELD OF THE INVENTION

The present invention relates to processes for dehydrogenating alkanes to alkenes, specifically alkane dehydrogenation processes using a chromium oxide catalyst, a method for decreasing the temperature and/or increasing the efficiency of an alkane dehydrogenation process, and a composition formed by dehydrogenating an alkane with a chromium oxide catalyst.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Alkenes are one of the most important feedstocks for industrial chemical purposes, since they can participate in a wide variety of reactions. For example, ethylene and propylene can be polymerized to form polyethylene and polypropylene, respectively, and isobutylene can be reacted with methanol to form methyl tert-butyl ether (MTBE). Alkenes, however, are far less naturally abundant than their alkane counterparts.

Alkanes are obtained in abundant quantities as byproducts of fossil fuel refining processes, and are useful precursors for the more industrially relevant alkenes. For example, alkenes are produced from alkanes industrially by thermal cracking and steam cracking Alkanes also may be catalytically dehydrogenated to alkenes by the following endothermic reaction:

$$C_nH_{2n+2} \rightarrow C_nH_{2n} + H_2 \Delta H_R° > 0 \quad (R1)$$

Hydrogen-containing gases, such as $H_2$ and $CH_4$, are typically used in a reduction cycle, for example reducing the chromium from an oxidation state of $Cr^{6+}$ to $Cr^{3+}$ in a chromium oxide catalyst.

Because alkane dehydrogenation reactions are highly endothermic, they require high temperatures to obtain acceptable yields. However, these high temperatures enhance undesired side reactions, including the formation of carbonaceous coke deposits on the catalyst bed. Coke buildup adversely affects catalyst performance, leading to lower yields and expensive maintenance. For example, once catalysts have been deactivated by coke buildup, the dehydrogenation process must be taken offline and so that the catalyst may be regenerated, typically by burning off the coke deposits with air. This may also result in oxidation of the catalyst again requiring the use of a reduction cycle to form the active catalyst species such as a $Cr^{3+}$ composition. Time spent offline reduces overall reactor efficiency.

SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawing.

One aspect of the present invention includes a process of dehydrogenating an alkane to an alkene, including: (a) feeding an alkane feedstock and CO to a reactor containing a catalyst comprising $Cr_2O_3$; and (b) contacting the alkane feedstock with the catalyst to form an alkene and $H_2$; wherein, in the reactor: a portion of the CO fed to the reactor reduces the $CrO_3$ to form $Cr_2O_3$ and $CO_2$.

A second aspect of the present invention includes a process of dehydrogenating an alkane to an alkene, including: (a) feeding an alkane feedstock and CO to a reactor containing (i) a catalyst comprising $Cr_2O_3$ and (ii) a heat-releasing material comprising CuO; and (b) contacting the alkane feedstock with the catalyst to form an alkene and $H_2$; wherein, in the reactor: a first portion of the CO fed to the reactor reduces the $CrO_3$ to form $Cr_2O_3$ and $CO_2$; and a second portion of the CO fed to the reactor reduces the CuO to form Cu and $CO_2$.

A third aspect of the present invention includes a process of dehydrogenating an alkane to an alkene, including: (a) feeding an alkane feedstock and a first amount of CO to a reactor containing a catalyst comprising $Cr_2O_3$; and (b) contacting the alkane feedstock with the catalyst to form an alkene and $H_2$; wherein, in the reactor: a portion of the first amount of CO fed to the reactor reduces the $CrO_3$ to form $Cr_2O_3$ and a portion of the $CO_2$ reacts with the $H_2$ to form $H_2O$ and a second amount of CO; and a portion of the second amount of CO reduces the $CrO_3$ to form $Cr_2O_3$ and $CO_2$.

A fourth aspect of the present invention includes a process of dehydrogenating an alkane to an alkene, including: (a) feeding an alkane feedstock and a first amount of CO to a reactor containing (i) a catalyst comprising $Cr_2O_3$ and (ii) a heat-releasing material comprising CuO; and (b) contacting the alkane feedstock with the catalyst to form an alkene and $H_2$; wherein, in the reactor: a first portion of the first amount of CO fed to the reactor reduces the $CrO_3$ to form $Cr_2O_3$ and $CO_2$; a second portion of the first amount of CO fed to the reactor reduces the CuO to form Cu and $CO_2$; a portion of the $CO_2$ reacts with the $H_2$ to form $H_2O$ and a second amount of CO; a first portion of the second amount of CO reduces the $CrO_3$ to form $Cr_2O_3$ and $CO_2$; and a second portion of the second amount of CO reduces the CuO to form Cu and $CO_2$.

In another aspect of the process of dehydrogenating an alkane to an alkene, the alkane feedstock includes a $C_2$-$C_{10}$ alkane.

In another aspect of the process of dehydrogenating an alkane to an alkene, the alkane feedstock includes a $C_3$-$C_5$ alkane.

In another aspect of the process of dehydrogenating an alkane to an alkene, the alkane feedstock includes isobutane.

In another aspect of the process of dehydrogenating an alkane to an alkene, the catalyst comprising $Cr_2O_3$ comprise an alumina or zirconia support.

A fifth aspect of the invention includes an alkene-containing composition obtained by dehydrogenating an alkane in the presence of a chromium oxide catalyst.

A sixth aspect of the invention includes a chromium oxide-containing catalyst obtained by regenerating a catalyst with CO.

BRIEF DESCRIPTION OF THE DRAWING

A more complete appreciation of the disclosure and many of the attendant advantages thereof will be readily obtained as the same becomes better understood by reference to the following detailed description when considered in connection with the accompanying drawing, wherein.

DETAILED DESCRIPTION OF THE INVENTION

Figure 1:
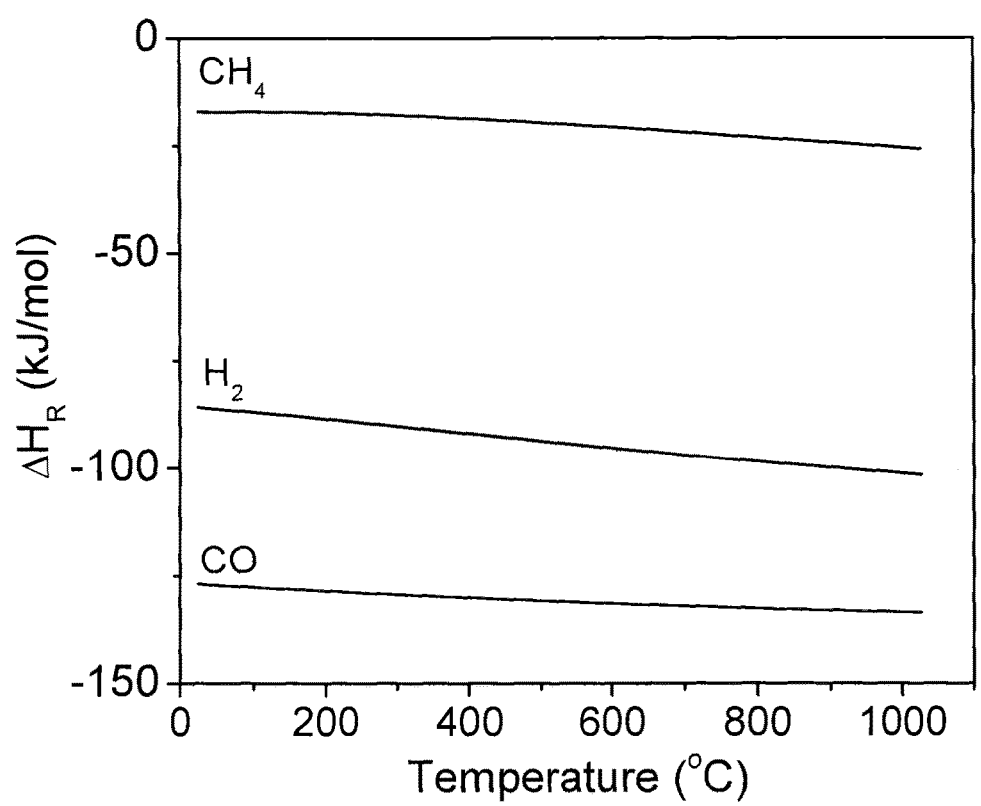
FIG. 1 shows a graph comparing enthalpy of reaction with CuO versus temperature, for three reducing gases CO, $H_2$ and $CH_4$.

Conventional processes for catalytically dehydrogenating an alkane to an alkene use hydrogen-containing gases, such as $H_2$ and $CH_4$, in a reduction cycle to reduce the catalyst. Aspects of the present invention instead use CO as a reducing gas to reduce the catalyst, during the dehydrogenation reaction. As shown below, and as shown by thermochemical analysis, using CO as a reducing gas for the reduction cycle of a dehydrogenation process can provide more heat to the reactor bed than using $H_2$. This additional heat can aid in the endothermic dehydrogenation reaction of an alkane to an alkene.

The enthalpy change for the reduction of $CrO_3$ with $H_2$ was calculated based on standard enthalpies of formation:

$$CrO_3(s)+3/2H_2(g) \rightarrow \tfrac{1}{2}Cr_2O_3(s)+3/2H_2O(g) \Delta H_R^\circ = -336 \text{ kJ/mol} \quad (R2)$$

wherein kJ/mol is kiloJoules per mole.

The enthalpy change for the reduction of $CrO_3$ with CO similarly was calculated based on standard enthalpies of formation:

$$CrO_3(s)+3/2CO(g) \rightarrow \tfrac{1}{2}Cr_2O_3(s)+3/2CO_2(g) \Delta H_R^\circ = -397 \text{ kJ/mol} \quad (R3)$$

Both reduction reactions are highly exothermic. However, based on the calculations, reducing $CrO_3$ with CO provides an approximately 18% greater enthalpy change compared to reducing $CrO_3$ with $H_2$ based on crystalline $CrO_3$.

Because of the greater enthalpy change in reducing $CrO_3$ with CO compared to reducing $CrO_3$ with $H_2$, CO may be advantageously used to reduce in situ a chromium oxide catalyst used in an endothermic alkane dehydrogenation reaction. The additional heat produced by reducing $CrO_3$ with CO and retaining the heat in a reactor means less energy needs to be supplied when performing a concurrent alkane dehydrogenation in the reactor. In aspects of the invention, additional heat in an amount of 2 to 20%, preferably 4 to 18%, 6 to 16%, 8 to 14% or 10 to 12%, based on the total enthalpy of the reduction of $CrO_3$ to $Cr_2O_3$ with CO, in comparison with the reduction of $CrO_3$ with $H_2$, is obtained. The use of CO as a reducing gas to reduce a $CrO_3$ catalyst provides other benefits in addition to the enthalpic benefit described above. When an alkane is dehydrogenated to its corresponding alkene, other undesired alkanes and alkenes, as well as coke, may be produced as decomposition byproducts. For example, the dehydrogenation of isobutane (i-$C_4H_{10}$) to form isobutene (i-$C_4H_8$) may also produce decomposition byproducts including propane ($C_3H_8$), propylene ($C_3H_6$), ethane ($C_2H_6$), ethylene ($C_2H_4$), and methane ($CH_4$) by the following reactions:

$$\text{i-}C_4H_{10} \rightarrow \text{i-}C_4H_8+H_2 \quad (R4)$$

$$\text{i-}C_4H_{10}+H_2 \rightarrow C_3H_8+CH_4 \quad (R5)$$

$$C_3H_8 \rightarrow C_3H_6+H_2 \quad (R6)$$

$$2CH_4 \rightarrow C_2H_6+H_2 \quad (R7)$$

$$C_3H_8 \rightarrow C_2H_4+CH_4 \quad (R8)$$

$$C_2H_6 \rightarrow C_2H_4+H_2 \quad (R9)$$

The production of these decomposition byproducts requires the presence of hydrogen (see, e.g., reaction (R5)). Accordingly, it is advantageous in the present invention to provide an alternate reaction pathway for hydrogen, so that decomposition reactions such as (R5) to (R9), as well as coke formation, are suppressed or eliminated. In aspects of the invention, the yield of any of $CH_4$, $C_3H_6$, $C_3H_8$, $C_2H_6$, or $C_2H_4$ during the dehydrogenation of isobutane (i-$C_4H_{10}$) to form isobutene, is less than 0.1 volume percent (vol %), preferably less than 0.05 vol %, 0.001 vol %, 0.0005 vol %, 0.0001 vol %, 0.00005 vol % or less than 0.00001 vol % based on the total volume of the isobutane subjected to the dehydrogenation reaction.

As described above, reducing $CrO_3$ with CO in the present invention results in the production of $CO_2$, as shown in reaction (R3). This $CO_2$ may be used as a scavenger to react with hydrogen produced in the concurrent alkane dehydrogenation reaction, thereby decreasing the amount of hydrogen available for facilitating decomposition reactions such as (R5) to (R9), and decreasing coke formation. The reaction of $CO_2$ with $H_2$ proceeds via the reverse water-gas shift reaction, as follows:

$$CO_2(g)+H_2(g) \rightarrow CO(g)+H_2O(g) \Delta H_R^\circ = +41 \text{ kJ/mol} \quad (R10)$$

Decreasing the amount of hydrogen available in the dehydrogenation reactor in this way provides the additional benefit of shifting the equilibrium of the dehydrogenation reaction (R1) toward the product side, further improving reactor performance Additionally, the CO produced in the reverse water-gas shift reaction can be recycled to reduce the chromium oxide catalyst, according to reaction (R3).

In certain aspects of the present invention, the reactor contains a heat-releasing material comprising CuO, in addition to the catalyst comprising $Cr_2O_3$. Such a heat-releasing material provides heat to the endothermic dehydrogenation reaction via the highly exothermic reduction reaction of CuO with CO.

According to thermodynamic analysis, the reduction process using CO with CuO at 298K (R11) produces extra heat of approximately 48% compared to $H_2$ (R12). Thus the pre-heating cost for the dehydrogenation can be reduced. Alternatively, the amount of heat-generating materials can be reduced if the heat capacity in the reactor bed is fixed at a certain reaction temperature. Furthermore, similar to the $Cr^{6+}$ reduction process (R3) the product gas is $CO_2$. Thus it can be used as another source for the in situ scavenger of hydrogen via the reverse water-gas shift (RWGS) reaction (R10). As shown in reactions (R12) and (R13), the reduction of CuO with $H_2$ or $CH_4$ does not produce $CO_2$, and the exothermicities of these reactions are lower than that of CO (R11).

$$CuO(s)+CO(g) \rightarrow Cu(s)+CO_2(g) \Delta H_R(298 \text{ K})=-127 \text{ kJ/mol} \quad (R11)$$

$$CuO(s)+H_2(g) \rightarrow Cu(s)+H_2O(g) \Delta H_R(298 \text{ K})=-86 \text{ kJ/mol} \quad (R12)$$

$$CuO(s)+\tfrac{1}{3}CH_4(g) \rightarrow Cu(s)+2/3H_2O(g)+\tfrac{1}{3}CO(g) \Delta H_R(298 \text{ K})=-17 \text{ kJ/mol} \quad (R13)$$

As shown in FIG. 1, thermodynamic analysis reveals that the heat released by reducing CuO with CO is much higher than that released by reducing CuO with either $H_2$ or $CH_4$, not only at a temperature of 298K in (R11) to (R13), but also a higher temperature suitable for alkane dehydrogenation.

The inventive alkane dehydrogenation process may be performed continuously or in a batch operation. In a batch operation, the process may begin with a fresh catalyst comprising $Cr_2O_3$. During the dehydrogenation reaction, the $CrO_3$ may be contacted with CO to form $Cr_2O_3$. Alternatively, the batch process may begin with partially or fully spent catalyst comprising $CrO_3$, which is initially contacted with CO to form $Cr_2O_3$ prior to performing the alkane dehydrogenation reaction. In an exemplary embodiment more than 90% by mass, preferably more than 95% or 99% by mass of the chromium in the fresh catalyst is in the form of $Cr_2O_3$. Subsequent use in a dehydrogenation process may lower the amount of Cr present as $Cr_2O_3$ in the catalyst to form a spent catalyst in which from 40% by mass or less, preferably from 50%, 60%, 70%, 80% or 90% by mass or less of the chromium is in the form of $Cr_2O_3$. Concurrent regeneration of the spent catalyst with CO forms a catalyst in which more than 90% by mass, preferably more than 95% or 99% by mass of the chromium is in the form of $Cr_2O_3$.

Figure 2:
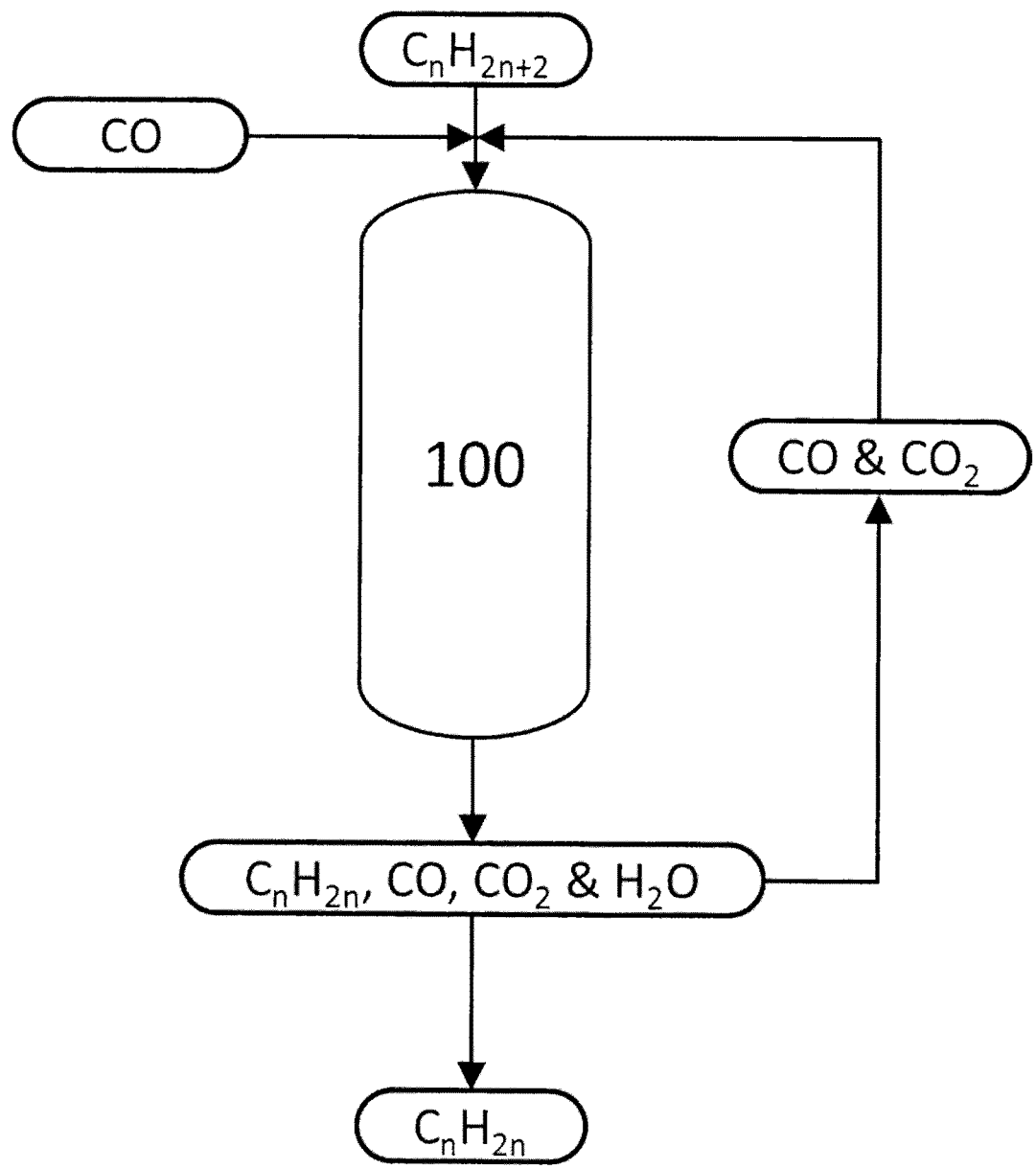
FIG. 2 shows a schematic diagram of an alkane dehydrogenation process according to an embodiment of the invention.

A non-limiting embodiment of a continuous process according to the third aspect of the invention is shown in FIG. 2. This process includes a reactor 100 containing a catalyst comprising $Cr_2O_3$. An alkane feedstock is fed to the reactor 100, along with CO. The alkane in the alkane feedstock is dehydrogenated in the reactor 100 by contacting the alkane feedstock with the $Cr_2O_3$ catalyst to form an alkene and $H_2$ according to reaction (R1) above. The CO fed to the reactor 100 is contacted with the $CrO_3$ to form $Cr_2O_3$ and $CO_2$. Any excess, unreacted CO exits the reactor 100, along with $CO_2$ produced according to reaction (R3) above. The CO and $CO_2$ are separated, and the CO and $CO_2$ may be recycled to the feed for the reactor 100.

The $CO_2$ produced in the reactor 100 and any $CO_2$ recycled to the reactor 100 reacts with some or all of the $H_2$ in the reactor 100 to form CO and $H_2O$, via the reverse water-gas shift reaction (R4) above. Additional $CO_2$, that is, $CO_2$ not produced in the reactor 100 or recycled to the reactor 100, may also be supplied to the reactor 100. The alkene, CO and $H_2O$ produced in the reactor 100 exit the reactor and are separated. The CO from the reactor 100 may be recycled to the feed for the reactor 100.

Although FIG. 2 depicts a single reactor performing catalytic dehydrogenation concurrently with catalyst regeneration, another aspect of the invention includes multiple reactors operating in parallel. One or more reactors may perform the catalytic dehydrogenation while one or more reactors undergo maintenance.

The amount of CO fed to the reactor containing a catalyst comprising $CrO_3$ may vary depending on the amount of the catalyst in the reactor, and the extent of conversion from $Cr_2O_3$ to $CrO_3$ in the catalyst. Preferably, CO is fed to the reactor at a space velocity of about 0.014 l/s based on the catalyst bed volume, and/or at a gas volumetric flow rate of about 2.5 cubic meters per second ($m^3/s$) based on the mass of the catalyst.

The amount of $CO_2$ produced in the reactor by reducing the $CrO_3$ with CO may vary depending on the amount of the catalyst in the reactor, and the flow rate of CO into the reactor. Additional $CO_2$ may be supplied to the reactor, to augment the $CO_2$ produced by reducing the $CrO_3$ with CO. The amount of additional CO2 is preferably from 0.1 to 100 times the amount of $CO_2$ produced by reducing the $CrO_3$ with CO, more preferably from 1 to 50 times, or 5 to 10 times.

The temperature in the reactor during the alkane dehydrogenation may vary depending on the flow rates of alkane and CO into the reactor, and the mass of the catalyst. Preferably, the temperature in the reactor is about 580° C., and the pressure in the reactor is about 1 atmosphere (atm).

The alkane feedstock fed to the reactor performing the alkane dehydrogenation may be derived from a fossil fuel refining process, and may be supplied from a liquefied petroleum gas source. The alkane feedstock is preferably fed to the reactor in a gas or vapor phase. The alkane contains one or more alkanes, and may contain one or more non-alkane species, such as alkenes and/or alkynes. The alkane in the feedstock may be a straight-chain alkane or a branched alkane. It is preferably a $C_2$-$C_{10}$ alkane, more preferably a $C_3$-$C_5$ alkane, more preferably isobutane. The alkene produced in the dehydrogenation reaction is preferably a $C_2$-$C_{10}$ alkene, more preferably a $C_3$-$C_5$ alkene, more preferably isobutene.

The amount of the alkane fed to the reactor performing the alkane dehydrogenation may vary depending on the amount of the catalyst in the reactor, the amount of CO and $CO_2$ fed to the reactor with the alkane, and the temperature in the reactor. Preferably, the alkane feedstock is fed to the reactor at a space velocity of 0.12 l/s based on the catalyst bed volume, and/or a gas volumetric flow rate of 22.2 $m^3/s$ based on the mass of the catalyst.

The catalyst comprising $Cr_2O_3$ used for the alkane dehydrogenation preferably comprises a support component in addition to the chromium component. The support component may comprise silica, alumina, boria, magnesia, thoria, titania, zirconia, or mixtures of two or more thereof. The support component preferably comprises alumina, zirconia or both. The support may be a zeolite or modified zeolite. The support component preferably has a surface area of 50 to 700 square meters per gram, more preferably 400 to 600 square meters per gram ($m^2/g$), and preferably has a pore volume of 0.5 to 4 cubic centimeters per gram ($m^3/g$), more preferably 2 to 3 cubic centimeters per gram.

The chromium component can be combined with the support component in various manners, such as, for example, forming a co-precipitated tergel of silica, titanium, and chromium. Alternatively, an aqueous solution of a water soluble chromium component can be added to a hydrogel of the support component. Suitable water soluble chromium components include, but are not limited to, chromium nitrate, chromium acetate, and chromium trioxide. Alternatively, a solution of a hydrocarbon soluble chromium component such as tertiary butyl chromate, a diarene chromium compound, biscyclopentadienyl chromium (II), or chromium acetyl acetonate, can be used to impregnate a zerogel, which results from removal of water from a cogel. The chromium component is preferably used in an amount sufficient to give about 10 weight percent chromium, more preferably about 20 weight percent chromium, based on the total weight of the chromium component and the support component.

The catalyst is preferably arranged in a fixed bed configuration in the reactor. The catalyst may be used to perform the alkane dehydrogenation reaction for as long as the catalyst retains cost-efficient catalytic activity.

The single-pass conversion of the alkane in the dehydrogenation reactor is preferably 35% or greater, more preferably 40% or greater, 45% or greater, 50% or greater, 55% or greater, 60% or greater, 65% or greater, 70% or greater, 75% or greater, 80% or greater, 85% or greater, 90% or greater, or 95% or greater. Unreacted alkane may be separated from the product stream leaving the dehydrogenation reactor, for example by an alkane-alkene splitter, and recycled to the feed entering the reactor. The overall conversion of the alkane is preferably 70% or greater, 75% or greater, 80% or greater, 85% or greater, 90% or greater, 95% or greater, 96% or greater, 97% or greater, 98% or greater, or 99% or greater. The selectivity of the alkane to the desired alkene (for example, the selectivity of isobutane to isobutene) is preferably 50% or greater, more preferably 55% or greater, 60% or greater, 65% or greater, 70% or greater, 75% or greater, 80% or greater, 85% or greater, 90% or greater, 95% or greater, 96% or greater, 97% or greater, 98% or greater, or 99% or greater.

The reactor can contain a heat-releasing material comprising CuO, in addition to the catalyst comprising $Cr_2O_3$. Such a heat-releasing material provides heat to the endothermic dehydrogenation reaction via the highly exothermic reduction reaction of CuO with CO. The heat-releasing material comprising CuO preferably comprises a support component in addition to the CuO component. The support component may comprise silica, alumina, boria, magnesia, thoria, titania, zirconia, or mixtures of two or more thereof. The support material may be a zeolite. The support component preferably comprises alumina, zirconia or both. The support component preferably has a surface area of 50 to 700 square meters per gram, more preferably 400 to 600 square meters per gram, and preferably has a pore volume of 0.5 to 4 cubic centimeters per gram, more preferably 2 to 3 cubic centimeters per gram.

Disclosed herein is a process of catalytically dehydrogenating an alkane to an alkene, using $Cr_2O_3$ as a catalyst, where the catalyst is reduced (e.g., concurrently) with the dehydrogenation by using CO as a reducing gas. In reducing the catalyst with CO, $CO_2$ is produced, which may be reacted with $H_2$ produced by the dehydrogenation, to form CO and $H_2O$ by the reverse water-gas shift reaction. A CuO heat-releasing material may be included with the catalyst in the reactor. The CO reducing gas reduces CuO to form Cu and $CO_2$, releasing heat. The $CO_2$ produced by reducing the CuO may also be reacted with $H_2$ produced by the dehydrogenation, to form CO and $H_2O$ by the reverse water-gas shift reaction.

Set forth below are some embodiments of the process disclosed herein.

Embodiment 1: A process of dehydrogenating an alkane to an alkene, comprising: feeding an alkane feedstock and a first amount of CO to a reactor (e.g., a dehydrogenation reactor) containing a catalyst comprising $Cr_2O_3$; and contacting the alkane feedstock with the catalyst to form an alkene and $H_2$. During the contacting: a first portion of the first amount of CO fed to the reactor reduces the $CrO_3$ to form $Cr_2O_3$ and $CO_2$; a portion of the $CO_2$ reacts with the $H_2$ to form $H_2O$ and a second amount of CO; and a first portion of the second amount of CO reduces the $CrO_3$ to form $Cr_2O_3$ and $CO_2$.

Embodiment 2: A process of dehydrogenating an alkane to an alkene, comprising: feeding an alkane feedstock and a first amount of CO to a reactor containing a catalyst comprising $Cr_2O_3$ and a heat-releasing material comprising CuO; and contacting the alkane feedstock with the catalyst to form an alkene and $H_2$. During the contacting: a first portion of the first amount of CO fed to the reactor reduces the $CrO_3$ to form $Cr_2O_3$ and $CO_2$; a second portion of the first amount of CO fed to the reactor reduces the CuO to form Cu and $CO_2$; a portion of the $CO_2$ reacts with the $H_2$ to form $H_2O$ and a second amount of CO; a first portion of the second amount of CO reduces the $CrO_3$ to form $Cr_2O_3$ and $CO_2$; and a second portion of the second amount of CO reduces the CuO to form Cu and $CO_2$.

Embodiment 3: The process of any of Embodiments 1-2, wherein the alkane feedstock comprises a $C_2$-$C_{10}$ alkane.

Embodiment 4: The process of any of Embodiments 1-3, wherein the alkane feedstock comprises a $C_3$-$C_5$ alkane.

Embodiment 5: The process of any of Embodiments 1-4, wherein the alkane feedstock comprises isobutane.

Embodiment 6: The process of any of Embodiments 1-5, wherein the catalyst further comprises an alumina or zirconia support.

Embodiment 7: The process of any of Embodiments 1-6, wherein a single-pass conversion of the alkane in the reactor is 55% or greater; preferably 75% or greater; preferably, 80% or greater, and preferably 90% or greater.

Embodiment 8: The process of any of Embodiments 1-7, wherein the alkane feedstock is fed to the reactor at a space velocity of 0.12 $s^{-1}$ based on the catalyst bed volume.

Embodiment 9: The process of any of Embodiments 1-8, wherein the process lowers an amount of Cr present as $Cr_2O_3$ in the catalyst such that 40% by mass or less of the chromium is in the form of $Cr_2O_3$, preferably 60% or less; preferably 80% or less.

Embodiment 10: The process of any of Embodiments 1-9, further comprising separating the CO and the $CO_2$, and recycling to the reactor at least one of the separated CO and the separated $CO_2$ to the reactor.

Embodiment 11: The process of any of Embodiments 1-10, further comprising concurrent regeneration the catalyst with CO, wherein the regeneration forms a regenerated catalyst in which more than 90% by mass of chromium in the catalyst is in the form of $Cr_2O_3$; preferably more than 95% by mass; or preferably more than 99% by mass.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

This application claims the benefit of U.S. Provisional Patent Application Ser. No. 62/085,234 filed Nov. 26, 2014, which is incorporated herein by reference in its entirety.

The invention claimed is:

1. A process of dehydrogenating an alkane to an alkene, comprising:
    feeding an alkane feedstock and a first amount of CO to a reactor containing a catalyst comprising $Cr_2O_3$; and
    contacting the alkane feedstock with the catalyst to form an alkene and $H_2$;
    wherein, during the contacting:
        a first portion of the first amount of CO fed to the reactor reduces the $CrO_3$ to form $Cr_2O_3$ and $CO_2$;
        a portion of the $CO_2$ reacts with the $H_2$ to form $H_2O$ and a second amount of CO; and
        a first portion of the second amount of CO reduces the $CrO_3$ to form $Cr_2O_3$ and $CO_2$.

2. The process of claim 1, wherein the reactor further contains a heat-releasing material comprising CuO; and further wherein, during the contacting:
  a second portion of the first amount of CO fed to the reactor reduces the CuO to form Cu and $CO_2$; and
  a second portion of the second amount of CO reduces the CuO to form Cu and $CO_2$.

3. The process of claim 1, wherein the alkane feedstock comprises a $C_2$-$C_{10}$ alkane.

4. The process of claim 1, wherein the alkane feedstock comprises a $C_3$-$C_5$ alkane.

5. The process of claim 1, wherein the alkane feedstock comprises isobutane.

6. The process of claim 1, wherein the catalyst further comprises an alumina or zirconia support.

7. The process of claim 1, further comprising concurrent regeneration the catalyst with CO, wherein the regeneration forms a regenerated catalyst in which more than 90% by mass of chromium in the catalyst is in the form of $Cr_2O_3$.

8. The process of claim 1, further comprising concurrent regeneration the catalyst with CO, wherein the regeneration forms a regenerated catalyst in which more than 95% by mass of chromium in the catalyst is in the form of $Cr_2O_3$.

9. The process of claim 1, further comprising concurrent regeneration the catalyst with CO, wherein the regeneration forms a regenerated catalyst in which more than 99% by mass of chromium in the catalyst is in the form of $Cr_2O_3$.

10. A process of dehydrogenating an alkane to an alkene, comprising:
  feeding an alkane feedstock and a first amount of CO to a reactor containing a heat-releasing material comprising CuO and a catalyst comprising $Cr_2O_3$;
  contacting the alkane feedstock with the catalyst to form an alkene and $H_2$; and
  concurrently regenerating the catalyst with CO, wherein the regeneration forms a regenerated catalyst in which more than 90% by mass of chromium in the catalyst is in the form of $Cr_2O_3$;
  wherein, during the contacting:
    a first portion of the first amount of CO fed to the reactor reduces the $CrO_3$ to form $Cr_2O_3$ and $CO_2$;
    a second portion of the first amount of CO fed to the reactor reduces the CuO to form Cu and $CO_2$;
    a portion of the $CO_2$ reacts with the $H_2$ to form $H_2O$ and a second amount of CO;
    a first portion of the second amount of CO reduces the $CrO_3$ to form $Cr_2O_3$ and $CO_2$; and
    a second portion of the second amount of CO reduces the CuO to form Cu and $CO_2$.

11. The process of claim 10, wherein the alkane feedstock comprises a $C_2$-$C_{10}$ alkane.

12. The process of claim 11, wherein the alkane feedstock comprises a $C_3$-$C_5$ alkane.

13. The process of claim 10, wherein the alkane feedstock comprises isobutane.

14. The process of claim 10, wherein the catalyst further comprises an alumina or zirconia support.

15. The process of claim 10, further comprising concurrent regeneration the catalyst with CO, wherein the regeneration forms a regenerated catalyst in which more than 95% by mass of chromium in the catalyst is in the form of $Cr_2O_3$.

16. The process of claim 10, further comprising concurrent regeneration the catalyst with CO, wherein the regeneration forms a regenerated catalyst in which more than 99% by mass of chromium in the catalyst is in the form of $Cr_2O_3$.

17. The process of claim 1, further comprising supplying additional $CO_2$ to the reactor in an amount of 0.1 to 100 times the amount of $CO_2$ produced by reducing the $CrO_3$ with CO.

18. The process of claim 1, further comprising supplying additional $CO_2$ to the reactor in an amount of 1 to 50 times the amount of $CO_2$ produced by reducing the $CrO_3$ with CO.

19. The process of claim 1, further comprising supplying additional $CO_2$ to the reactor in an amount of 5 to 10 times the amount of $CO_2$ produced by reducing the $CrO_3$ with CO.

\* \* \* \* \*